United States Patent [19]

Camiener

[11] Patent Number: 5,439,667
[45] Date of Patent: Aug. 8, 1995

[54] METHOD FOR PRESERVING TISSUE FOR MICROSCOPIC EXAMINATION USING AN OSMOTICALLY CONTROLLED GLYOXAL SOLUTION

[76] Inventor: Gerald W. Camiener, 26700 Hurlingham Rd., Beachwood, Ohio 44122

[21] Appl. No.: 160,285

[22] Filed: Dec. 2, 1993

Related U.S. Application Data

[63] Continuation of Ser. No. 762,307, Sep. 20, 1991, abandoned.

[51] Int. Cl.$^6$ ............................................. A01N 1/02
[52] U.S. Cl. ....................... 435/40.5; 424/75; 435/1; 435/2; 435/40.52; /
[58] Field of Search ............. 435/1, 2, 3; 424/75, 424/3

[56] References Cited

U.S. PATENT DOCUMENTS

| | | | |
|---|---|---|---|
| 2,333,182 | 11/1943 | Jones et al. | 424/75 |
| 4,136,161 | 1/1979 | Falkowski | 424/3 |
| 4,857,300 | 8/1989 | Maksem | 435/1 |
| 4,946,669 | 8/1990 | Siegfried et al. | 424/3 |
| 5,001,047 | 3/1991 | Liberman | 435/1 |

FOREIGN PATENT DOCUMENTS 3319564 12/1984 Germany ................................. 435/1

OTHER PUBLICATIONS

Yanoff et al. "Glutaraldehyde Fixation of Whole Eyes," *The American Journ. of Clin Pathology*. vol. 44(2), 1965. pp. 167–171.

*Primary Examiner*—David M. Naff
*Assistant Examiner*—L. Blaine Lankford

[57] ABSTRACT

Methods are provided to prepare a variety of tissues in a pathology-stable form for microscopic examination by preserving the tissue with an aqueous solution of $C_{2-6}$ dialdehyde and/or dialdehyde addition products, including glyoxal and/or glutaraldehyde in an amount sufficient to prevent autolysis and other degradative changes. The solution may further contain alcohols, chelating agents, buffers and acids. In one embodiment, the aqueous solution contains glyoxal or glyoxal in the form of a bisulfite, hydrate or alcohol addition product and an osmotic controlling ionic and/or nonionic chemical. This solution prevents degradation of tissue without substantial cross-linking.

11 Claims, No Drawings

METHOD FOR PRESERVING TISSUE FOR MICROSCOPIC EXAMINATION USING AN OSMOTICALLY CONTROLLED GLYOXAL SOLUTION

This application is a continuation of U.S. application Ser. No. 07/762,307 filed Sep. 20, 1991, now abandoned.

BACKGROUND OF THE INVENTION

The prior art is replete with formaldehyde treatments for various purposes. Chang et al., U.S. Pat. No. 4,654,312, teaches a composition for destroying erythrocytes while maintaining leukocytes that comprises formaldehyde. In a representative composition, Example 1, discloses 1% formaldehyde, 3% ethylene glycol and 0.25% sodium citrate at a pH 7.7±0.5 Chang et al. describe this as a "lysing solution" (col. 5, line 33). It is also stated by Chang et al. in a generic disclosure that in lieu of formaldehyde they contemplate about 0.5 to about 4 percent of any short chain aliphatic aldehyde, but preferably formaldehyde (col. 3, line 65—col. 4, line 2). It is stated that this aldehyde acts as a fixing agent to stabilize the white cells while the distilled water that is in the mixture acts as a lysing agent to rupture the erythrocytes. While Chang et al. disclose that their composition destroys erythrocytes, Falkowski et al., U.S. Pat. No. 4,136,161, disclose that glyoxal with sodium titrate serves to stabilize erythrocytes. There is no suggestion of the use of an alkanol with the glyoxal. It is also to he noted that contrary to the teachings of Falkowski et al., while monovalent ions such as potassium are indicated in the prior art as useful for stabilization of glutaraldehyde, research that has been conducted subsequently has shown that the aldehyde is destroyed and not saved by the potassium ion treatment. Buchalter, U.S. Pat. No. 3,983,252, discloses at col. 7, Example 1, a 50% aqueous solution, 40 cc. glutaraldehyde with 7 gm sodium citrate and 50 cc propylene glycol, and 960 cc water. The use of this composition is as a disinfectant, with no suggestion of providing histological stabilization. In a generic recitation of various other ingredients, glyoxal is included as a recitation of one of the aldehydes that might be used. Jones, U.S. Pat. No. 2,333,182, at Example 1, discloses a mixture of 37% water, 30% glyoxal at 40% strength and 20% methanol, with a use as an embalming fluid. Rendon, U.S. Pat. No. 3,057,775, in Examples 1 and 3 discloses an aqueous mixture of an alkanol, glutaraldehyde, sodium acetate as well as phenol, glycerin, and a wetting agent for use as an embalming fluid. Specific use of glyoxal is not suggested. Ryan, U.S. Pat. No. 4,198,206, discloses stabilization of platelet with the use of glutaraldehyde, and suggests that ethylene glycol is used as an "antifreeze" i.e. to protect against freezing of the stabilizing solution, col. 1, lines 42–47.

DETAILED DESCRIPTION

In accordance with a first aspect of the invention there is provided a method of providing pathology-stable tissue which comprises treating said tissue with an aqueous solution (I) of a $C_{2-6}$ dialdehyde and/or dialdehyde addition product in an amount sufficient to prevent major degenerative changes in said tissue, whereby said tissue remains in a state suitable for micro-, or macroscopic examination sufficient for pathological or experimental examination.

Preferred embodiments comprise glyoxal and glutaraldehyde as the $C_{2-6}$ dialdehyde, which may be used alone or in admixture with other components. In one embodiment, the $C_{2-6}$ dialdehyde is an aldehyde addition product in the form of a bisulfite, hydrate or alcohol addition product. When the $C_{2-6}$ dialdehyde is an aldehyde addition product in the form of a bisulfite, hydrate, alcohol, or glycol addition product, the addition product may be used alone as a liquid form, or in the solid form to which water and/or an alkanol can be added to provide a liquid mixture, or in combination with other materials. When the bisulfite is used, it is preferably in the form of an metal salt, preferably the sodium or potassium salt. When in the form of an alcohol addition product, the addition product used is preferably a glycol such as ethylene glycol, the product of which is known as dioxanediol. The use of a solid form of a dialdehyde is particularly advantageous for kits in that leakage, shipping, and stability problems are eliminated. Water and/or an alkanol is added by the user shortly before a sample is added to the kit.

Tissues suitable for dialdehyde treatment include tissues of animal, or plant origin, but particularly those of mammalian and human origin.

In one embodiment, said $C_{2-6}$ dialdehyde is present in an amount of from about 0.08% to about 36% of the overall solution. More preferably, said $C_{2-6}$ dialdehyde is present in an amount of from about 0.2% to about 20% percent of the overall solution. Also included within the solution may be from about 0.15% to about 36% of a $C_{1-4}$ alkane-mono- di- or triol. Alkanols include monools like ethanol, diols like ethylene glycol and triols like glycerol. Glycerol is particularly suited for a stabilizing solution (I) that has as one of its objectives the maintenance of a tissue sample in a more pliable condition. Mono- and diol-alkanes are particularly useful in permitting faster tissue penetration of the stabilizing solution which is very important for preserving of larger tissue samples and organs. Mono- and diol-alkanes also are particularly effective in stabilizing dialdehydes in solution, thereby providing active reactants for longer times.

In another preferred embodiment, the stabilizing solution is prepared by mixing an appropriate amount of dialdehyde bisulfite addition product in water, together with sodium or potassium phosphates, to give a pH of 7.3. The resulting pH buffered stabilizing solution maintains physiologic conditions while it is stabilizing the tissue, is preventing autolysis, and is maintaining the tissue in a condition suitable for pathology observation. In a preferred embodiment, said solution includes at least one $C_{1-4}$ alkane mono-, di- or triol at a concentration of from about 0.4% to about 32% of said solution, whereby the penetration of said solution into said tissue is facilitated. In a further embodiment, said solution includes an ionic or nonionic chemical in an amount of from about 0.1% to about 14% of said solution, whereby the osmotic pressure effects of said solution is altered, thereby modifying and/or stabilizing said tissue for subsequent examination. In one such embodiment, sea lamprey eels are stabilized using a dialdehyde solution containing 3% sodium chloride.

In other embodiments, additional and specific microanatomical stabilization effects are obtained by the inclusion of various specific reactants including mercuric salts, trichloroacetic acid, acetic acid, picric acid and potassium dichromate, in amounts of from abut 0.07% to about 40.0%. In one preferred embodiment, said dialdehyde solution contains 37% picric acid, and 5% glacial acetic acid. Another preferred embodiment, said dialdehyde solution contains 4.5% mercuric chloride, 0.5% sodium chloride and 2% trichloracetic acid. Other reactants can include chromium trioxide, copper salts, and various other heavy-metal and transition-metal salts.

In a further aspect of the invention, there is provided a method for simultaneously providing a pathology-stable tissue while decalcifying calcified regions within said tissue wherein said solution includes an acid and or acid-salt such as formic, hydrochloric, citric and nitric acids and/or their alkali-metal or ammonium salt forms in amount of from about 0.3% to about 75%. In this embodiment, for the simultaneous preservation of a pathology-stable tissue and decalcification of any calciferous regions within said tissue, the solution may additionally, or alternatively, include a chelating agent, in an amount from about 0.1% to about 18%, such as ethylene-diamine-tetra-acetic acid, or an alkali-metal-salt or ammonium-salt thereof.

By a "pathology-stable tissue," there is intended to mean that a tissue sample has been stabilized in a state suitable for pathology and/or experimental examination. In such a stabilized condition, the microscopic and macroscopic cell, tissue and organ constituents will have been maintained in as lifelike a condition as possible, substantially free from the autolytic and other changes that occur when normal tissue is removed from a living being or organism (as in the case of a biopsy sample), or when the entire body or organism dies and a portion of the body is to be preserved for subsequent examination. As the term is used herein, a "tissue" refers to any form of tissue, whether a thin slice taken, for example, from a possibly cancerous tissue for purpose of a biopsy, or any larger portion that includes such tissue, for example, a liver or a kidney. By applying the solution as soon as possible after removal or death, the application of the solution (I) serves to stabilize the tissue in as normal as possible a state, and immediately stops metabolic reactions, autolytic changes and microbial degradative changes. Autolysis is a process whereby the normal cellular enzymes and components degrade and destroy the cell structure itself.

In a further aspect of the invention there is provided a kit for maintaining a pathology-stable preparation which comprises a female receptacle means and a male closure means, and contained within said female receptacle means an aqueous solution containing a $C_{2-6}$ dialdehyde and/or dialdehyde addition product in an amount sufficient to prevent major degenerative changes in the sample reserved for pathological examination. Such a kit also can contain a solid form of a dialdehyde addition product to which water and/or alkanol is added prior to the sample being introduced. The stabilizing solution also can contain various other pH buffering and osmotic-pressure affecting chemicals, as well as various special-effect reactants as described earlier.

In one embodiment, the kit is for maintaining a stool sample in a stabilized form so that parasites, worms and/or protozoans contained in the stool sample are maintained in a condition suitable for analysis and evaluation at a later time by an appropriate laboratory. Said kit includes a female receptacle means and a male closure means and a stabilizing solution containing $C_{2-6}$ dialdehyde and/or dialdehyde addition product. In an embodiment, said tissue is in the form of an organ or an entire organism which is to be preserved for a prolonged period of time, whereby said solution prevents substantial degenerative changes within this period. Other embodiments employ said kit for the collection, stabilization, and maintenance of other bodily fluids, solids, exudates and/or secretions such as phlegm, mucous, semen, pus and urine.

In a further aspect of the invention, there is provided a composition capable of providing pathology-stable tissue when a tissue is immersed in said composition, said composition being an aqueous solution of a $C_{2-6}$ dialdehyde and/or dialdehyde addition product in an amount sufficient to prevent major degenerative changes in said tissue, said $C_{2-6}$ dialdehyde being present in an amount of from about 0.08% to about 36% percent of the overall solution, and said solution including from about 0.15% to about 36% of a $C_{2-4}$ alkane- mono-, di-, or triol to stabilize said solution. In this aspect, a further embodiment provides a solution that includes at least one $C_{2-4}$ mono-, di-, or triol alkane at a concentration of from about 0.4% to about 32% of said solution, whereby the penetration of said solution into said tissue is facilitated. In this embodiment, preferably said solution includes an ionic or nonionic chemical in an amount of from about 0.1% to about 14% of said solution, whereby the osmotic pressure effects of said solution is altered, thereby stabilizing said tissue for subsequent examination. A further embodiment, the preferably said solution contains an acid and/or an acid-salt and/or a chelating agent to effect decalcification of calcified portions of tissues.

In one embodiment of this first aspect of the invention there is provided a small sample of tissue from either a biopsy or a fresh cadaver that is treated with the solution (I) in an amount sufficient to prevent autolysis of the tissue by native enzymes that upon cessation of living state of the tissue operate to digest and to disintegrate the tissue, and to prevent other degenerative changes in the tissue.

In a further embodiment of this first aspect of the invention, there is provided a test-stable stool sample kit comprising means for maintaining a stool sample in a condition for evaluation at a later time by an appropriate laboratory including a female receptacle means and a male closure means and the stabilizing solution (I). As a typical female receptacle means may be mentioned wide mouth jar containers of plastic or glass or the like with a screw pattern to accommodates a male screw cap closure. Another female receptacle means could be a bag or pouch, and the "male" closure could be a tie or clamp. It is to be understood that the female receptacle means may be of any shape, size or form provided it is such as to accommodate a sample of tissue, organ or bodily product that is to be inserted into the female receptacle means.

While various fixatives are known in the art, the stabilizing solution (I) reacts quickly with a variety of groups in the cell to stop enzyme actions, to fix structural features, to stop microbial actions and generally to maintain the sample in a manner as close to the form and appearance of the living tissue as possible, whereby the pathology examination is facilitated.

In a second aspect of the invention, the stabilizing solution (I) is used to prepare parts or whole animals or plants in an anatomically preserved state for a prolonged period of time, and compositions useful in that method. The stabilizing solution (I) of the invention may be used to preserve frogs or other small animals for school laboratory dissection, or entire cadavers or individual organs for medical school instructional and other uses. The stabilizing solution (I) also facilitates the preservation of the specimen by killing and/or inhibiting any microorganisms that otherwise might be present or develop and thereby degrade the specimen.

Whereas in the first aspect of the invention, stabilization of a tissue sample was desired for a period of days, in this second aspect of the invention, stabilization for a prolonged period preferably measured in years, is the object. It is intended to be used with specimens such as frogs, fetal pigs, cadavers, cats, worms, insects or large organs that are to be used for study or dissection whether in a high school, college medical school, or autopsy setting, or other preservation uses.

It should be noted that the tissue may be of animal or plant origin. While human tissue, organs, or the entire organism are contemplated, it should be noted that the invention is contemplated as applicable to any mammal, amphibian, reptile, bird, bony fish, cartilaginous fish, insect, arthropod, cephlapod, insect, mutilcellular microorganism, round worm, flat worm, segmented worm or any other animal or plant group. Depending on the specific application, it may be desirable to include at least one additional chemical such as mercuric salts, trichloroacetic acid, acetic acid, picric acid, potassium dichromate, phenol, biphenol, phenols, cresols, quaternary ammonium compounds, surfactants, antibiotics copper salts, sulfosalicylic acid, osmic acid, platinum salts, cadmium salts, cobalt salts and uranyl salts. Generally, the amount of any of these additional chemicals would be from about 0.07% to about 16.5%.

The following examples illustrate the invention:

EXAMPLE 1.

To a glass container, there is added 100 ml of a 40% solution of glyoxol and 900 ml of deionized water. With mixing, 4.0 g of sodium acid phosphate monohydrate and 6.5 g of anhydrous disodium phosphate are added and dissolved. The pH is approximately neutral. Small pieces of dog tissue are immersed in the solution for several hours, and then are processed for histological examination. Good cellular detail is observed, with no evidence of autolysis or other degradative changes.

EXAMPLE 2.

To a glass container, there is added 800 ml of deionized water and 100 ml of a 10% solution of anhydrous calcium chloride. 100 ml of a 50% glutaraldehyde solution is added with mixing, and the resulting solution is stored over marble chips. The pH is approximately 6. Small pieces of human tissue are immersed in the solution for 24 hours and processed for histological examination. Good cellular detail is observed without evidence of cellular autolysis, cellular distortion, or phospholipid "myelin forms".

EXAMPLE 3.

To a glass container, there is added, in order with mixing, 700 ml 4 of deionized water, 200 ml of denatured ethyl alcohol and 150 ml of a 40% glyoxal solution. Kidneys are cut in half so that one-end serves as a control for the other end. Kidney halves are immersed in at least 10 times their volume of the said prepared solution and allowed to stand for varying periods of time. They then are prepared for pathological and histological examination. After 6 hours of exposure to the solution, the center-most portions of the kidney show good penetration of the solution whilst the controls that were immersed in the same solution without ethyl alcohol show very much poorer penetration in the center-most portions.

EXAMPLE 4.

Kidneys prepared and treated in accordance with Example 3 are examined after 7 and 21 days of immersion in said solution. The kidneys remain in good stabilized condition suitable for pathologic and histologic examination. Good cellular detail is observed, without observable degradative changes.

EXAMPLE 5.

To a glass container, there is added, in order with mixing, 700 ml of deionized water, 200 ml of ethylene glycol and 100 ml of a 40% glyoxal solution. The solution is adjusted to pH 7.3 by the dropwise addition of sodium hydroxide solution under conditions of continuous mixing. The solution is stored for a few days and then is used to stabilize pieces of human tissue prior to histologic processing and examination. Tissues processed with said solution show good preservation and cellular detail. Control tissues treated with the same solution absent the ethylene glycol show poorer preservation. Independent chemical analysis shows that the ethylene-glycol-containing solution has a higher dialdehyde concentration than the solution absent the ethylene glycol.

EXAMPLE 6.

To a glass container, there is added, in order with mixing, 500 ml of deionized water, 200 ml of denatured ethyl alcohol, 150 ml of glycerol, 60 ml of a 40% glyoxal solution, and 50 ml of a 50% solution of glutaraldehyde. Intact rat livers are separated into individual lobes and the lobes are used as controls for different experimental conditions. In this example, lobes were immersed for 14 days in 10-fold excesses of said solution. The lobes are then processed and examined. Lobes treated with said solution show good preservation and good tissue consistency with no evidence of "crumbliness." Control lobes immersed in the same solution absent the glycerol did not show the same tissue "pliability" and "softness." Microscopic examination of the test lobes treated with the solution in this example showed good cellular and microcellular detail. Control lobes treated with same solution except that the combination of dialdehydes was not used also show good cellular detail, but the uptake of stain was not as uniform in some subcellular details as was seen when the combination of dialdehydes was used.

EXAMPLE 7.

To a glass container, there is added, in order with mixing, 850 ml of denatured ethyl alcohol, 50 ml of glacial acetic acid and 100 ml of a 40% glyoxal solution. Various arachnids, insects and plant parts were immersed in said solution and were examined after one week, three weeks and nine months of immersion. All tissues, cells and organisms showed good preservation and good cellular detail.

EXAMPLE 8.

To a glass container, there is added, in order with mixing, 800 ml of deionized water, 45 g mercuric chloride, 5 g of sodium chloride, 20 g of trichloroacetic acid, 40 ml of glacial acetic acid, and 200 ml of 40% glyoxal solution. Pieces of mammalian tissued are immersed in the solution for 3 to 24 hours. Slices less than 2 mm in thickness need only 3 hours of treatment. Subsequent processing and examination showed good preservation and good cellular detail with negligible shrinkage of connective tissue.

EXAMPLE 9.

To a glass container, there is added, in order with mixing, 850 ml of deionized water, 10 g of formic acid, 100 g of trisodium citrate, and 100 ml of a 40% glyoxal solution. Pieces of mammalian bone are immersed in at least a 10-fold excess of said solution and left for 5-7 days. Subsequent processing and examination show good preservation and good cellular detail. Calcified areas are completely decalcified and shrinkage is not observed.

EXAMPLE 10.

The formic acid and sodium citrate in Example 9 were replaced with 100 g of disodium ethylene-diamine tetraacetate. Mammalian teeth were immersed in said modified solution and left for 7-10 days. Subsequent processing and examination showed good preservation and good structure Decalcification appears to complete.

EXAMPLE 11.

A test-stable stool sample kit is provided which includes means for maintaining a stool sample in a condition suitable for analysis at a later time by an appropriate laboratory include a female receptacle means and a male closure means and 30 ml. of an aqueous solution which contains 40% glyoxal. As a typical female receptacle means may be mentioned a 2 oz. wide mouth plastic container with a screw pattern to accommodates a male screw cap closure. It is to be understood that the female receptacle means may be of any shape, size or form provided it is such to accommodate a small scraping of bowel sample that is to be inserted into the female receptacle means.

Parasites which may be in the stool sample and which may be an object of laboratory examination are preserved in the stool samples to permit the stool sample to be properly used to identify the presence of such parasites.

EXAMPLE 12.

In the test-stable stool sample kit of Example 11, the mentioned aqueous solution is replaced by 800 mg of dioxanediol (solid), which is dissolved in 20 ml of an aqueous solution prior to inserting the stool sample. Parasites which may be in the stool sample and which may be an object of laboratory examination are preserved in the stool samples to permit the stool sample to be properly used to identify the presence of such parasites.

EXAMPLE 13.

In the test-stable stool sample kit of Example 11, the mentioned aqueous solution is replaced by an aqueous solution containing 30 ml. of an aqueous solution which contains 20% glutaraldehyde. Protozoan parasites which may be in the stool sample and which may be an object of laboratory examination are preserved in the stool samples to permit the stool sample to be properly used to identify the presence of such parasites.

EXAMPLE 14.

A freshly excised primate heart is perfused with a solution of glyoxal as prepared in Example 5 except that the pH was not adjusted. Following perfusion, the heart was left immersed in a closed container for 10 months, and then examined macroscopically and microscopically. The heart is preserved in good condition with no apparent degradative changes, and is suitable for student observation.

EXAMPLE 15.

An adult bull frog is extinguished under ether, and is perfused with the solution described in Example 14 to which sodium chloride (0.6%) and cetyltrimethylammonium bromide (0.15%) have been added. The frog is kept moistened with same solution (under wetted cotton) in a closed container. The frog remains suitable for student dissection for a period of at least one year.

What is claimed is:

1. A method of preserving multicellular tissue for microscopic examination without substantially cross-linking the tissue, which comprises:

contacting the tissue with an aqueous solution consisting essentially of (i) about 0.08% to about 36% glyoxal or glyoxal in the form of a bisulfite, hydrate or alcohol addition product and (ii) about 0.1% to about 14% of an osmotic controlling ionic or nonionic chemical or a combination of osmotic controlling ionic or nonionic chemicals, wherein the glyoxal is present in a concentration sufficient to prevent degradation of the tissue prior to microscopic examination without substantially cross-linking the tissue and the osmotic controlling chemical or combination of osmotic controlling chemicals is present in a concentration sufficient to osmotically stabilize the tissue for subsequent microscopic examination, and examining the tissue under a microscope.

2. The method as claimed in claim 1 wherein the glyoxal is in the form of an addition product.

3. The method as claimed in claim 1 wherein the tissue is selected from the group consisting of animal and plant tissue.

4. The method as claimed in claim 1 wherein the glyoxal is present in an amount from about 0.2% to about 20% of the overall solution.

5. The method as claimed in claim 1 wherein the tissue is in the form of an organ or an entire organism.

6. The method of claim 3 wherein the tissue is mammalian tissue.

7. A method of preserving multicellular tissue for microscopic examination without substantially cross-linking the tissue, which comprises:

contacting the tissue with an aqueous solution consisting essentially of (i) about 0.08% to about 36% glyoxal or glyoxal in the form of a bisulfite, hydrate or alcohol addition product, (ii) about 0.15% to about 36% of a $C_{1-4}$ alkane mono-, di-, or triol, and (iii) about 0.1% to about 14% of an osmotic controlling ionic or nonionic chemical or a combination of osmotic controlling ionic or nonionic chemicals, wherein the glyoxal is present in a concentration sufficient to prevent degradation of the tissue prior to microscopic examination without substantially cross-linking the tissue and the osmotic controlling chemical or combination of osmotic controlling chemicals is present in a concentration sufficient to osmotically stabilize the tissue for subsequent microscopic examination, and examining the tissue under a microscope.

8. A method of preserving multicellular tissue for microscopic examination without substantially cross-linking the tissue, which comprises:

contacting the tissue with an aqueous solution consisting essentially of (i) about 0.08% to about 36% glyoxal or glyoxal in the form of a bisulfite, hydrate or alcohol addition product, (ii) about 0.01 moles/liter to about 4.2 moles/liter of a pH buffering agent, and (iii) about 0.1% to about 14% of an osmotic controlling ionic or nonionic chemical or a combination of osmotic controlling ionic or nonionic chemicals, wherein the glyoxal is present in a concentration sufficient to prevent degradation of the tissue prior to microscopic examination without substantially cross-linking the tissue and the osmotic controlling chemical or combination of osmotic controlling chemicals is present in a concentration sufficient to osmotically stabilize the tissue for subsequent microscopic examination, and examining the tissue under a microscope.

9. A method of preserving multicellular tissue for microscopic examination without substantially cross-linking the tissue, which comprises:

contacting the tissue with an aqueous solution consisting essentially of (i) about 0.08% to about 36% glyoxal or glyoxal in the form of a bisulfite, hydrate or alcohol addition product, (ii) about 0.3% to about 75% of an acid selected from the group consisting of formic, hydrochloric, citric, and nitric acids, their alkali-metal salts, their ammonium salts, and combinations thereof, and (iii) about 0.1% to about 14% of an osmotic controlling ionic or nonionic chemical or a combination of osmotic controlling ionic or nonionic chemicals, wherein the glyoxal is present in a concentration sufficient to prevent degradation of the tissue prior to microscopic examination without substantially cross-linking the tissue, the acid is present in a concentration sufficient to decalcify calcified regions within the tissue, and the osmotic controlling chemical or combination of osmotic controlling chemicals is present in a concentration sufficient to osmotically stabilize the tissue for subsequent microscopic examination, and examining the tissue under a microscope.

10. A method of preserving multicellular tissue for microscopic examination without substantially cross-linking the tissue, which comprises:

contacting the tissue with an aqueous solution consisting essentially of (i) about 0.08% to about 36% glyoxal or glyoxal in the form of a bisulfite, hydrate or alcohol addition product, (ii) about 0.1% to about 18% of a chelating agent, and (iii) about 0.1% to about 14% of an osmotic controlling ionic or nonionic chemical or a combination of osmotic controlling ionic or nonionic chemicals, wherein the glyoxal is present in a concentration sufficient to prevent degradation of the tissue prior to microscopic examination without substantially cross-linking the tissue and the osmotic controlling chemical or combination of osmotic controlling chemicals is present in a concentration sufficient to osmotically stabilize the tissue for subsequent microscopic examination, and examining the tissue under a microscope.

11. A method of preserving multicellular tissue for microscopic examination without substantially cross-linking the tissue, which comprises:

contacting the tissue with an aqueous solution consisting essentially of (i) about 0.08% to about 36% glyoxal or glyoxal in the form of a bisulfite, hydrate or alcohol addition product, (ii) heavy metal or transition metal salts, and (iii) about 0.1% to about 14% of an osmotic controlling ionic or nonionic chemical or a combination of osmotic controlling ionic or nonionic chemicals, wherein the glyoxal is present in a concentration sufficient to prevent degradation of the tissue prior to microscopic examination without substantially cross-linking the tissue and the osmotic controlling chemical or combination of osmotic controlling chemicals is present in a concentration sufficient to osmotically stabilize the tissue for subsequent microscopic examination, and examining the tissue under a microscope.

* * * * *